United States Patent
Yun et al.

(10) Patent No.: US 11,035,050 B2
(45) Date of Patent: Jun. 15, 2021

(54) ELECTROPLATING COMPOSITION AND ELECTROPLATING METHOD

(71) Applicant: SOULBRAIN CO., LTD., Seongnam-si (KR)

(72) Inventors: Jong Cheol Yun, Seongnam-si (KR); Wan Joong Kim, Seongnam-si (KR); Hee Jeong Ryu, Seongnam-si (KR); Seung Min Park, Seongnam-si (KR)

( * ) Notice: Subject to any disclaimer, the term of this patent is extended or adjusted under 35 U.S.C. 154(b) by 75 days.

(21) Appl. No.: 16/226,620

(22) Filed: Dec. 19, 2018

(65) Prior Publication Data

US 2020/0123671 A1    Apr. 23, 2020

(30) Foreign Application Priority Data

Oct. 23, 2018  (KR) .................. 10-2018-0126478
Dec. 12, 2018  (KR) .................. 10-2018-0159597

(51) Int. Cl.
| | |
|---|---|
| *C25D 3/02* | (2006.01) |
| *C25D 3/38* | (2006.01) |
| *C07D 473/38* | (2006.01) |
| *C07D 239/48* | (2006.01) |
| *C07D 239/58* | (2006.01) |

(52) U.S. Cl.
CPC ............. *C25D 3/38* (2013.01); *C07D 239/48* (2013.01); *C07D 239/58* (2013.01); *C07D 473/38* (2013.01)

(58) Field of Classification Search
CPC .................................. C25D 3/02; C25D 3/38
USPC ........................ 205/261, 297, 298
See application file for complete search history.

(56) References Cited

U.S. PATENT DOCUMENTS

| | | | | |
|---|---|---|---|---|
| 2,862,861 A * | 12/1958 | Moy | ............... | C25D 3/40 205/293 |
| 2003/0102226 A1* | 6/2003 | Gabe | ............... | C25D 3/38 205/263 |
| 2008/0268138 A1* | 10/2008 | Reddington | ............ | C25D 3/56 427/96.1 |
| 2013/0206602 A1* | 8/2013 | Lee | ............... | C25D 3/56 205/253 |
| 2017/0044671 A1* | 2/2017 | Milum | ............... | C23C 18/1844 |

OTHER PUBLICATIONS

Tang et al, "4,6-Dimethyl-2-Mercaptopyrimidine as a Potential Leveler for Microvia Filling with Electroplating Copper," RSC Adv.(2017), vol. 7, pp. 40342-40353. (Year: 2017).*

* cited by examiner

*Primary Examiner* — Edna Wong
(74) *Attorney, Agent, or Firm* — Jongkook Park

(57) ABSTRACT

The present invention relates to a electroplating composition and an electroplating method using the same. The electroplating composition of the present invention comprising a first leveling agent and a second leveling agent, wherein the first leveling agent and the second leveling agent each, independently, comprise a compound represented by Chemical Formula 1 below:

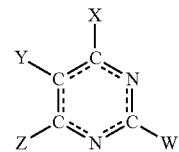

[Chemical Formula 1]

10 Claims, 2 Drawing Sheets

ELECTROPLATING COMPOSITION AND ELECTROPLATING METHOD

CROSS-REFERENCE TO RELATED APPLICATIONS

This application claims priority under 35 U.S.C. § 119 to Korean Patent Application No. 10-2018-0126478 filed on Oct. 23, 2018, and Korean Patent Application No. 10-2018-0159597, filed on Dec. 12, 2018, in the Korean Intellectual Property Office, the disclosure of which is incorporated herein by reference in its entirety.

TECHNICAL FIELD

The present invention relates to an electroplating composition and electroplating method using the same.

BACKGROUND

As interconnections become multilayered during the manufacture of a semiconductor device, features with high aspect ratios, e.g., vias or trenches, are formed on a substrate. The features are charged by electroplating with an electroplating composition. At this time, to minimize defects such as voids and seams, additives such as accelerators, suppressors, or leveling agents may be included in the electroplating composition.

During the process of electroplating using an electroplating composition containing an accelerator, bumps are formed due to the influence of the accelerator. As the plating process proceeds, an aggregation of bumps is formed as the bumps grow. At such a time, due to the accelerated formation of the bumps on regions with high aspect ratios and high density, like the features, a bigger aggregation is formed. Such a phenomenon is called overplating. The areas where overplating has occurred form steps from the surrounding regions, and the steps so formed cause defects in semiconductor devices due to increase of the processing time required during the chemical mechanical polishing process and impedance of surface smoothness.

Accordingly, a leveling agent is added to increase the smoothness of the surface. Conventionally, the use of polyethyleneimine, polyglycine, polyurea, polyacrylamide, polyaminoamide, polyalkanolamine, polyvinylpyridine, polyvinylpyrrolidone, copolymers of vinylimidazole and vinylpyrrolidone, and the like, as leveling agents has been disclosed.

However, such leveling agents still have limits to increasing surface smoothness, and thus various studies are being performed to further improve the smoothness of surfaces plating using electroplating compositions comprising leveling agents.

SUMMARY

An embodiment of the present invention is directed to providing an electroplating composition capable of exhibiting excellent smoothness of a plated surface.

To achieve the above-mentioned object, the present invention provides an electroplating composition comprising a first leveling agent and a second leveling agent, wherein the first leveling agent and the second leveling agent each, independently, comprise a compound represented by Chemical Formula 1 below:

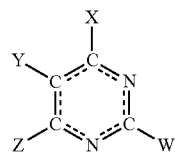

[Chemical Formula 1]

In Chemical Formula 1, X, Y, Z and W are each, independently, selected from the group consisting of hydrogen (—H), an alkyl group (—R), an amino group (—NH$_2$), a thiol group (—SH), and a hydroxyl group (—OH); or X and W are each, independently, selected from the group consisting of hydrogen, an alkyl group, an amino group, a thiol group, and a hydroxyl group, and Y and Z are each independently selected from the group consisting of H, C, O, N, S, Se, and Si as atoms included in the same heterocyclic ring; or Z and W are each, independently, selected from the group consisting of hydrogen, an alkyl group, an amino group, a thiol group, and a hydroxyl group, and X and Y are each, independently, selected from the group consisting of H, C, O, N, S, Se, and Si as atoms included in the same heterocyclic ring.

Further, the present invention provides an electroplating method comprising a step of contacting the electroplating composition with at least a portion of an object to be plated.

DETAILED DESCRIPTION OF EMBODIMENTS

Figure 1:
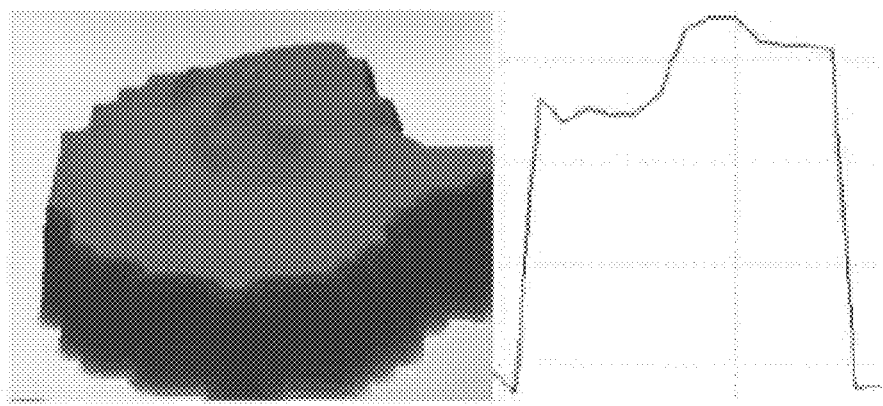
FIG. 1 shows an image of three-dimensional (3D) analysis of a plated layer formed using the electroplating composition of Example 2.

Hereinafter, the present invention is described.

The electroplating composition of the present invention comprises a first leveling agent and a second leveling agent.

The first leveling agent and the second leveling agent each, independently, comprise a compound represented by Chemical Formula 1 below. In view of improvement of smoothness, it is preferable to employ two or more leveling agents comprising the first leveling agent and the second leveling agent, which are different from each other, in the electroplating composition.

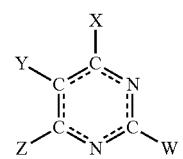

In Chemical Formula 1, X, Y, Z and W are each, independently, selected from the group consisting of hydrogen (—H), an alkyl group (—R), an amino group (—NH$_2$), a thiol group (—SH), and a hydroxyl group (—OH); X and W are each, independently, selected from the group consisting of hydrogen, an alkyl group, an amino group, a thiol group, and a hydroxyl group, and Y and Z are each independently selected from the group consisting of H, C, O, N, S, Se, and Si as atoms included in the same heterocyclic ring; or Z and W are each, independently, selected from the group consisting of hydrogen, an alkyl group, an amino group, a thiol group, and a hydroxyl group, and X and Y are each, independently, selected from the group consisting of H, C, O, N, S, Se, and Si as atoms included in the same heterocyclic ring.

In the present specification, the heterocyclic ring comprises, as a hetero atom, at least one atom selected from the group consisting of O, N, S, Se, and Si, and comprises a monocyclic ring or a polycyclic ring having 2 to 60 carbon atoms, which may be further substituted with other substituent groups. Herein, the term "polycyclic ring" means a group in which a heterocyclic ring is directly linked to other ring group or condensed therewith. Here, the other ring group may be a heterocyclic ring, but may also be other kinds of ring groups such as a cycloalkyl group, an aryl group, a heteroaryl group, and the like. Specific examples of the heterocyclic ring include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a triazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, a quinozolinyl group, a naphthyridil group, an acridinyl group, a phenanthridinyl group, an imidazopyridinyl group, a diazanaphthalene group, a triazaindene group, an indolyl group, an indolyzinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilol group, a spirobi(dibenzosilol), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacrylidinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrodibenzo [b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group, and the like, but the heterocyclic ring is not limited thereto.

In the present specification, the alkyl group (—R) includes linear or branched chains having 1 to 60 carbon atoms, which may be further substituted with other substituent groups. The number of carbon atoms of the alkyl group may be 1 to 60, specifically, 1 to 40, and more specifically, 1 to 20. Specific examples of the alkyl group may include a methyl group, an ethyl group, a propyl group, an n-propyl group, an isopropyl group, a butyl group, a n-butyl group, an isobutyl group, a tert-butyl group, a sec-butyl group, a 1-methylbutyl group, a 1-ethylbutyl group, a pentyl group, a n-pentyl group, a isopentyl group, a neopentyl group, a tert-pentyl group, a hexyl group, a n-hexyl group, a 1-methylpentyl group, a 2-methylpentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethylpropyl group, a 1,1-dimethylpropyl group, an isohexyl group, a 2-methylpentyl group, a 4-methylhexyl group, a 5-methylhexyl group, and the like, but the alkyl group is not limited thereto.

In the present specification, when X, Y, Z and W in Chemical Formula 1 are each an amino group, a thiol group, or a hydroxyl group, the bond to the pyrimidine ring may be represented by a single bond or a double bond according to a resonance structure of the compound represented by Chemical Formula 1, and it will be readily understood by those skilled in the art that the effects of the compounds according to the present invention are not limited to the represented forms of the single bond or the double bond. For example, when X in Chemical Formula 1 is a thiol group (—SH), X may also be represented by a thione group (=S) according to the resonance structure of the compound represented by Chemical Formula 1.

In an embodiment of the present invention, X may be an amino group, W may be a thiol group, and Y and Z each, independently, may be one selected from a group consisting of an amino group, a thiol group, and a hydroxy group.

In another embodiment of the present invention, X and W may be thiol groups, and Y and Z may be hydrogen.

In yet another embodiment of the present invention, X may be a thiol group, W may be hydrogen, and Y and Z may each be N, wherein they may be included in a 5-membered heterocyclic ring having 3 carbon atoms.

More specifically, the first leveling agent and the second leveling agent are different from each other, and each, independently, may be at least one selected from the compounds represented by Chemical Formulas 2 to 5 below.

[Chemical Formula 2]

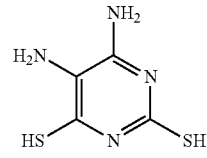

[Chemical Formula 3]

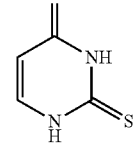

[Chemical Formula 4]

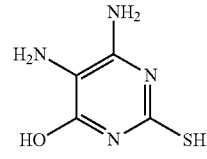

[Chemical Formula 5]

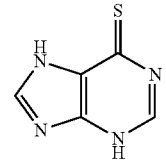

The present inventors found that when a pyrimidine-based compound containing a non-covalent electron pair was used as a leveling agent, it was effective in improving the smoothness of a plated layer since an excellent polarization effect was achieved at the time of electroplating. As a result of repeated studies on leveling agents having excellent smoothness, the present inventors could confirm that an electroplating composition comprising at least two kinds of leveling agents as described above had excellent smoothness.

More specifically, the present inventors found that as compared to an electroplating composition comprising one leveling agent, the electroplating composition comprising two kinds of leveling agents had much better smoothness even when the total amount of the leveling agents was the same, and thereby completed the present invention.

The electroplating composition of the present invention may comprise two or more leveling agents that are different from each other to achieve excellent smoothness.

Specifically, the weight ratio of the first leveling agent and the second leveling agent may be 1:9 to 9:1, and more specifically, 3:7 to 7:3. When the first leveling agent and the second leveling agent are used in the above-described weight ratio, the excellent degree of smoothness may be further improved.

In an embodiment, the weight ratio of the first leveling agent and the second leveling agent may be 1:1.

Further, the electroplating composition of the present invention may comprise a metal ion source and an electrolyte in addition to the first leveling agent and the second leveling agent.

The metal ion source supplies metal ions during the electroplating process. As the metal ion source, it is preferable to supply a monovalent metal cation, divalent metal cation, or a mixture thereof, and it is more preferable to supply a copper salt, but the metal ion source is not limited thereto.

The metal ion source may be at least one selected from a group consisting of sulfates, halides, acetates, citrates, borates, and sulfonates, and for example, may be one or more selected from a group consisting of copper sulfate, copper chloride, copper acetate, copper citrate, copper nitrate, copper fluoroborate, copper methane sulfonate, copper phenyl sulfonate and copper p-toluene sulfonate.

The amount of the metal ion source is not particularly limited, but may be 1% to 10% by weight based on the total weight of the electroplating composition, in consideration of the electroplating efficiency. In addition, when the electroplating composition comprises the metal ion source, the electrolyte, the first leveling agent, and the second leveling agent, the amount of the metal ion source may be 2% to 20% by weight, or, for example, more preferably 5% to 15% by weight, based on the total weight of the metal ion source, the electrolyte, the first leveling agent, and the second leveling agent. For example, when the amount of the metal ion source is less than or exceeds the above-described range based on the total amount of the metal ion source, the electrolyte, the first leveling agent, and the second leveling agent, metal ions may not be smoothly supplied or may be over-supplied at the time of electroplating, thereby causing defects such as voids and seams.

The electrolyte may serve to impart conductivity to the electroplating composition. The electrolyte is preferably an acidic electrolyte. Examples of the electrolyte may comprise at least one selected from the group consisting of sulfuric acid, acetic acid, fluoroboric acid, methanesulfonic acid, ethanesulfonic acid, propanesulfonic acid, trifluoromethanesulfonic acid, benzenesulfonic acid, p-toluenesulfonic acid, sulfamic acid, hydrochloric acid, hydrobromic acid, perchloric acid, nitric acid, chromic acid, and phosphoric acid, but the electrolyte of the present invention is not limited thereto.

The amount of the electrolyte is not particularly limited, but may be 1% to 10% by weight based on the total weight of the electroplating composition, in consideration of the electroplating efficiency. In addition, when the electroplating composition comprises the metal ion source, the electrolyte, the first leveling agent, and the second leveling agent, the amount of the electrolyte may be 2% to 20% by weight, or, for example, more preferably 5% to 15% by weight, based on the total weight of the metal ion source, the electrolyte, the first leveling agent, and the second leveling agent. For example, when the amount of the electrolyte is less than or exceeds the above-described range based on the total amount of the metal ion source, the electrolyte, the first leveling agent, and the second leveling agent, a local plating phenomenon may occur or the film quality may be deteriorated, and a problem in that defects occur on the plated layer during an annealing process may occur.

The first leveling agent and the second leveling agent control the smoothness of the plated surface in the electroplating process. The amount of the leveling agents is not particularly limited, but may be 0.1 g/L to 10 g/L, specifically, 0.01 g/L to 1 g/L or 0.001 g/L to 0.1 g/L, and more specifically, 0.0001 g/L to 0.03 g/L, based on the volume of the electroplating composition. In addition, when the electroplating composition comprises the metal ion source and the electrolyte, the amount of the leveling agents may be 2% by weight to 20% by weight, or, for example, more preferably 5% by weight to 15% by weight, based on the total weight of the metal ion source, the electrolyte, the first leveling agent, and the second leveling agent. For example, when the total amount of the leveling agents is less than the above-described range based on the total amount of the metal ion source, the electrolyte, the first leveling agent, and the second leveling agent, dimples may occur due to poor plating selectivity. When the total amount of the leveling agents exceeds the above-described range, problems may occur in that the plating may not be formed well on the plated layer due to excessive suppression, and dimples may be formed even if bottom-up electroplating is achieved.

In an embodiment, the electroplating composition according to the present invention may further comprise at least one of an accelerator and a suppressor to improve electroplating efficiency.

The accelerator increases the plating rate of metal ions in the electroplating process. Specific examples of the accelerator may be N,N-dimethyl-dithiocarbamic acid-(3-sulfopropyl)ester, 3-mercapto-propylsulfonic acid-(3-sulfopropyl)ester, 3-mercapto-propylsulfonic acid sodium salt, bis-sulfopropyl disulfide, bis-(sodium sulfopropyl)-disulfide, 3-(benzothiazolyl-s-thio)propyl sulfonic acid sodium salt, pyridinium propyl sulfobetaine, 1-sodium-3-mercapto propane-1-sulfonate, N,N-dimethyl-dithiocarbamic acid-(3-sulfoethyl)ester, 3-mercapto-ethylpropyl sulfonic acid-(3-sulfoethyl)ester, 3-mercapto-ethyl sulfonic acid sodium salt, bis-sulfoethyl disulfide, 3-(benzothiazolyl-s-thio)ethyl sulfonic acid sodium salt, pyridiniumethyl sulfobetaine, 1-sodium-3-mercaptoethane-1-sulfonate, mixtures thereof, and the like, but the accelerator is not limited thereto.

The amount of the accelerator is not particularly limited, but may be 0.0001 g/L to 0.02 g/L, and more specifically, 0.0005 g/L to 0.01 g/L, based on the volume of the electroplating composition, and preferably, 0.001 g/L to 0.005 g/L, based on the volume of the metal ion source, the electrolyte, and the leveling agents, in consideration of the electroplating efficiency. When the amount of the accelerator is less than 0.001 g/L based on the volume of the metal ion source, the electrolyte, and the leveling agents, the gloss of the plated surface may be lowered. When the amount of the accelerator exceeds 0.005 g/L, defects may occur due to initial excessive plating, and adhesion may be deteriorated.

The suppressor serves to suppress the rate of reduction of metal ions in the electroplating process, thereby controlling the rate at which the metal ions are plated. Specific examples of the suppressor may be poly ethylene glycol, poly propylene glycol, polyethylene glycol monoamine, polypropylene glycol monoamine, polyethylene glycol diamine, polypropylene glycol diamine, polyethylene glycol monothiol, polypropylene glycol monothiol, polyethylene glycol dithiol, polypropylene glycol dithiol, polyethylene glycol monoalkyl ether, polypropylene glycol monoalkylether, polyethylene glycol dialkylether, polypropylene glycol dialkyl ether, or copolymers of ethylene oxide and propyleneoxide, and the like, but the suppressor is not limited thereto.

The amount of the suppressor is not particularly limited, but may be 0.01 g/L to 1 g/L based on the volume of the electroplating composition, and preferably, 0.05 g/L to 0.8 g/L based on the volume of the metal ion source, the electrolyte, and the leveling agents, in consideration of the electroplating efficiency. When the amount of the suppressor is less than 0.05 g/L based on the volume of the metal ion source, the electrolyte, and the leveling agents, plating uniformity may not be good. When the amount of the suppressor exceeds 0.8 g/L, the plating rate may be lowered.

The electroplating composition may further comprise a residual amount of solvent, wherein the solvent may be water, alcohols or a mixture thereof. For example, in an embodiment, water may be used as the solvent.

The electroplating composition may further selectively comprise additives such as surfactants, anti-foaming agents, pH adjustors, and the like, that are known in the art, within a range in which the objects of the present invention are not impaired.

In one aspect, the present invention may provide an electroplating method comprising a step of contacting the electroplating composition with at least a portion of an object to be plated.

The object to be plated may be, but is not limited to, a damascene via, a panel, a printed circuit board (PCB), a through silicon via (TSV), or a bump.

Since the electroplating composition of the present invention comprises the above-described two or more leveling agents, when electroplating is performed using the electroplating composition, a plated surface having excellent smoothness may be obtained. In particular, the electroplating composition of the present invention may exhibit high smoothness when electroplating is performed on a feature in which the size of a gap between the features formed on a substrate is 5 to 100 µm and the aspect ratio of the feature is 1:0.5 to 1:10.

Preparation of Electroplating Composition

Preparation of Example 1

A copper plating composition was prepared to comprise 60 g/L of copper ions ($Cu2^+$) derived from copper sulfate, 60 g/L of sulfuric acid, 50 ppm of chloride ions, 2 ml/L of bis-sulfopropyl disulfide as an accelerator, 20 ml/L of PEG 8000 as a suppressor, 0.7 mg/L of a leveling agent represented by Chemical Formula 2, and 0.3 mg/L of a leveling agent represented by Chemical Formula 3 as a final combination.

Preparation of Example 2

A copper plating composition was prepared in the same manner as in Example 1, except that a mixture of 0.5 mg/L of the compound represented by Chemical Formula 2 and 0.5 mg/L of the compound represented by Chemical Formula 3 was used as the leveling agent.

Preparation of Example 3

A copper plating composition was prepared in the same manner as in Example 1, except that a mixture of 0.7 mg/L of the compound represented by Chemical Formula 2 and 0.3 mg/L of the compound represented by Chemical Formula 4 was used as the leveling agent.

Preparation of Example 4

A copper plating composition was prepared in the same manner as in Example 1, except that a mixture of 0.5 mg/L of the compound represented by Chemical Formula 2 and 0.5 mg/L of the compound represented by Chemical Formula 4 was used as the leveling agent.

Preparation of Example 5

A copper plating composition was prepared in the same manner as in Example 1, except that a mixture of 0.7 mg/L of the compound represented by Chemical Formula 2 and 0.3 mg/L of the compound represented by Chemical Formula 5 was used as the leveling agent.

Preparation of Example 6

A copper plating composition was prepared in the same manner as in Example 1, except that a mixture of 0.5 mg/L of the compound represented by Chemical Formula 2 and 0.5 mg/L of the compound represented by Chemical Formula 5 was used as the leveling agent.

Preparation of Example 7

A copper plating composition was prepared in the same manner as in Example 1, except that a mixture of 0.5 mg/L of the compound represented by Chemical Formula 3 and 0.5 mg/L of the compound represented by Chemical Formula 4 was used as the leveling agent.

Preparation of Example 8

A copper plating composition was prepared in the same manner as in Example 1, except that a mixture of 0.5 mg/L of the compound represented by Chemical Formula 3 and 0.5 mg/L of the compound represented by Chemical Formula 5 was used as the leveling agent.

Preparation of Example 9

A copper plating composition was prepared in the same manner as in Example 1, except that a mixture of 0.5 mg/L of the compound represented by Chemical Formula 4 and 0.5 mg/L of the compound represented by Chemical Formula 5 was used as the leveling agent.

Preparation of Comparative Example 1

A copper plating composition was prepared to comprise 60 g/L of copper ions ($Cu^{2+}$) derived from copper sulfate, 60 g/L of sulfuric acid, 50 ppm of chloride ions, 2 ml/L of bis-sulfopropyl disulfide as an accelerator, 20 ml/L of PEG 8000 as a suppressor, and 1 mg/L of a leveling agent represented by Chemical Formula 2 as a final combination.

Preparation of Comparative Example 2

A copper plating composition was prepared in the same manner as in Comparative Example 1, except that a compound represented by Chemical Formula 3 was used as the leveling agent.

Preparation of Comparative Example 3

A copper plating composition was prepared in the same manner as in Comparative Example 1, except that a compound represented by Chemical Formula 4 was used as the leveling agent.

Preparation of Comparative Example 4

A copper plating composition was prepared in the same manner as in Comparative Example 1, except that a compound represented by Chemical Formula 5 was used as the leveling agent.

TABLE 1

| | Leveling Agent (mg/L) | Leveling Agent (mg/L) | Dimple (μm) |
|---|---|---|---|
| Comparative Example 1 | Compound of Chemical Formula 2 1.0 | — | 2.7 |
| Comparative Example 2 | Compound of Chemical Formula 3 1.0 | — | 0.9 |
| Comparative Example 3 | Compound of Chemical Formula 4 1.0 | — | 1.1 |
| Comparative Example 4 | Compound of Chemical Formula 5 1.0 | — | 3.2 |
| Example 1 | Compound of Chemical Formula 2 0.7 | Compound of Chemical Formula 3 0.3 | −0.2 |
| Example 2 | Compound of Chemical Formula 2 0.5 | Compound of Chemical Formula 3 0.5 | −1.5 |
| Example 3 | Compound of Chemical Formula 2 0.7 | Compound of Chemical Formula 4 0.3 | 1.2 |
| Example 4 | Compound of Chemical Formula 2 0.5 | Compound of Chemical Formula 4 0.5 | 0.3 |
| Example 5 | Compound of Chemical Formula 2 0.7 | Compound of Chemical Formula 5 0.3 | 2.1 |
| Example 6 | Compound of Chemical Formula 2 0.5 | Compound of Chemical Formula 5 0.5 | 1.5 |
| Example 7 | Compound of Chemical Formula 3 0.5 | Compound of Chemical Formula 4 0.5 | −0.4 |
| Example 8 | Compound of Chemical Formula 3 0.5 | Compound of Chemical Formula 5 0.5 | 0.5 |
| Example 9 | Compound of Chemical Formula 4 0.5 | Compound of Chemical Formula 5 0.5 | 0.6 |

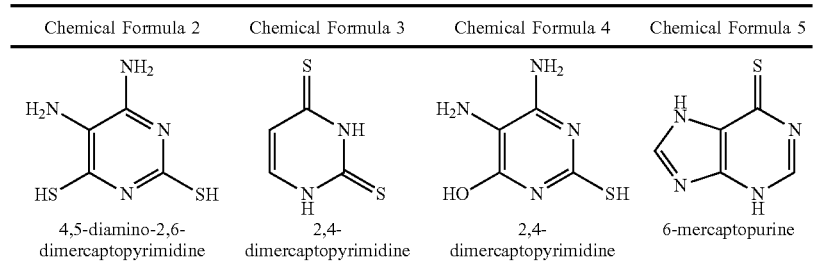

| Chemical Formula 2 | Chemical Formula 3 | Chemical Formula 4 | Chemical Formula 5 |
|---|---|---|---|
| 4,5-diamino-2,6-dimercaptopyrimidine | 2,4-dimercaptopyrimidine | 2,4-dimercaptopyrimidine | 6-mercaptopurine |

Evaluation of Plated Surface

Smoothness of the plated surface was evaluated by the following method using the above-prepared copper plating compositions.

Figure 2:
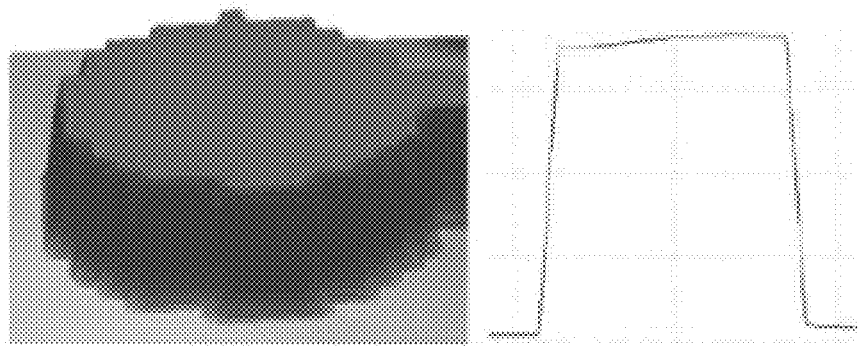
FIG. 2 shows an image of three-dimensional (3D) analysis of a plated layer formed using the electroplating composition of Example 4.
Figure 3:
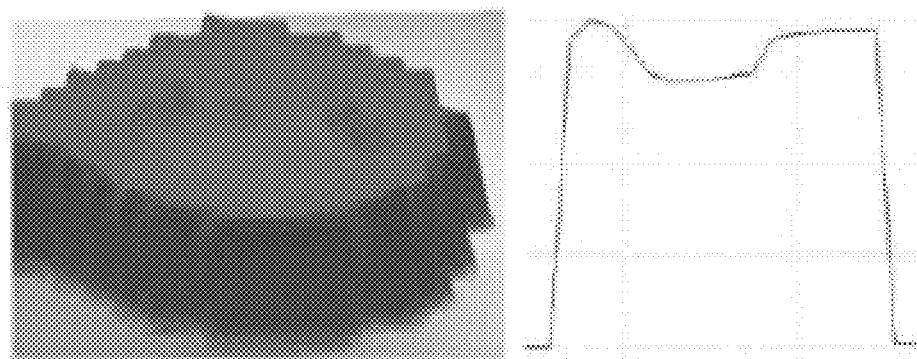
FIG. 3 shows an image of three-dimensional (3D) analysis of a plated layer formed using electroplating composition of Example 6.
Figure 4:
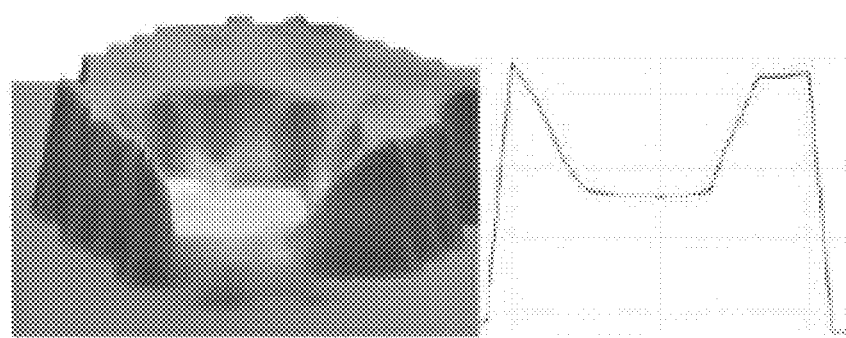
FIG. 4 shows an image of three-dimensional (3D) analysis of a plated layer formed using the electroplating composition of Comparative Example 1.

The plating substrate was manufactured by depositing copper seeds on a panel substrate with patterns having a diameter of 20 μm and a depth of 10 μm formed thereon. The plating substrate was immersed in the above-prepared electrolytic copper plating compositions, and then plated at a current density of 2 A/dm² to form a plated layer having a thickness of 5 μm. Dimples on the surface of the formed plated layer were measured using a three-dimensional (3D) optical surface profiler, and the results thereof are shown in Table 1 below. Three-dimensional (3D) analysis images of Comparative Example 1 and Examples 2, 4, and 6 are shown in FIGS. 1 to 4.

As can be seen from the results of Table 1 and FIGS. 1 to 4, it was confirmed that when the mixtures of compounds represented by Chemical Formulas 2 to 5 were used, remarkably excellent effects were obtained as compared to when the compounds were used alone. Further, it was confirmed that when the above-described combinations were used, a synergistic effect was obtained as compared to when the leveling agents were used alone.

Since the electroplating composition of the present invention comprises two or more compounds expressed by Chemical Formula 1 that are different from each other as a leveling agent, when electroplating is performed using the composition, an evenly leveled plated surface may be obtained. Accordingly, the present invention may allow even plating of a substrate with minimized defects, which may improve the reliability of semiconductor devices.

What is claimed is:

1. An electroplating composition comprising:
a first leveling agent and a second leveling agent,
wherein the first leveling agent is a compound represented by Chemical Formula 2, and the second leveling agent is one selected from the compounds represented by Chemical Formulas 3 to 5 below,
wherein the weight ratio of the first leveling agent to the second leveling agent is 3:7 to 7:3

[Chemical Formula 2]

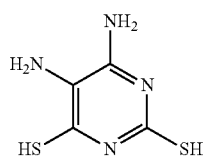

[Chemical Formula 3]

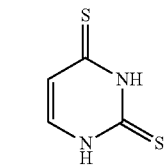

[Chemical Formula 4]

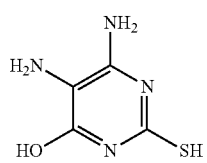

[Chemical Formula 5]

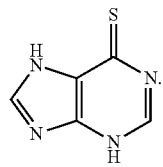

2. The electroplating composition of claim 1, wherein the amount of the leveling agents is 0.1 g/L to 10 g/L.

3. The electroplating composition of claim 1, further comprising a metal ion source and an electrolyte.

4. The electroplating composition of claim 3, wherein the metal ion source is at least one selected from the group consisting of copper sulfate, copper chloride, copper acetate, copper citrate, copper nitrate, copper fluoroborate, copper methane sulfonate, copper phenyl sulfonate and copper p-toluene sulfonate.

5. The electroplating composition of claim 3, wherein the electrolyte is at least one selected from the group consisting of sulfuric acid, acetic acid, fluoroboric acid, methanesulfonic acid, ethanesulfonic acid, propanesulfonic acid, trifluoromethanesulfonic acid, benzenesulfonic acid, p-toluenesulfonic acid, sulfamic acid, hydrochloric acid, hydrobromic acid, perchloric acid, nitric acid, chromic acid, and phosphoric acid.

6. The electroplating composition of claim 3, wherein the metal ion source supplies a monovalent metal cation, a divalent metal cation, or a mixture thereof.

7. The electroplating composition of claim 6, wherein the metal ion source is at least one selected from the group consisting of sulfates, halides, acetates, citrates, borates, and sulfonates.

8. The electroplating composition of claim 1, further comprising at least one of an accelerator and a suppressor.

9. The electroplating composition of claim 8, wherein an amount of the accelerator is 0.0001 g/L to 0.02 g/L based on the volume of the electroplating composition.

10. The electroplating composition of claim 8, wherein an amount of the suppressor is 0.01 g/L to 1 g/L based on the volume of the electroplating composition.

* * * * *